United States Patent [19]

Junino et al.

[11] Patent Number: 5,503,640
[45] Date of Patent: Apr. 2, 1996

[54] 3-SUBSTITUTED PARA-AMINOPHENOLS, PROCESS FOR PREPARING THEM, THEIR USE FOR DYEING KERATINOUS FIBRES AND THE INTERMEDIATE COMPOUNDS USED IN THE PREPARATION PROCESS

[75] Inventors: Alex Junino, Livry Gargan; Alain Genet, Aulnay sous Bois; Gerard Lang, Saint Gratien, all of France

[73] Assignee: L'Oreal, Paris, France

[21] Appl. No.: 249,923

[22] Filed: May 26, 1994

Related U.S. Application Data

[63] Continuation of Ser. No. 974,903, Nov. 12, 1992, Pat. No. 5,364,413, which is a continuation of Ser. No. 737,413, Jul. 29, 1991, abandoned, which is a division of Ser. No. 316,921, Feb. 28, 1989, Pat. No. 5,084,067.

[30] Foreign Application Priority Data

Mar. 3, 1988 [FR] France ................... 88 02713

[51] Int. Cl.$^6$ ............................ A61K 7/13; C07C 211/00
[52] U.S. Cl. ........................ 8/421; 8/405; 8/406; 8/408; 564/356; 564/442
[58] Field of Search ................. 8/405, 406, 421, 8/424, 408; 564/442, 443, 356

[56] References Cited

U.S. PATENT DOCUMENTS

| | | | |
|---|---|---|---|
| 3,893,803 | 7/1975 | Kaiser | 8/421 |
| 3,957,424 | 5/1976 | Zefren et al. | 8/421 |
| 4,164,704 | 10/1979 | Fakhouri | 8/421 |
| 4,473,374 | 9/1984 | Bugaut et al. | 8/405 |
| 4,662,892 | 5/1987 | Pike | 8/410 |
| 4,865,618 | 9/1989 | Junino et al. | 8/421 |
| 5,002,585 | 3/1991 | Junino et al. | 8/421 |

FOREIGN PATENT DOCUMENTS 8602829  5/1986  WIPO.

Primary Examiner—Prince Willis, Jr.
Assistant Examiner—James M. Silbermann
Attorney, Agent, or Firm—Cushman Darby & Cushman

[57] ABSTRACT

3-Substituted para-aminophenols of general formula:

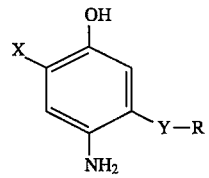

(I)

where
X=H, halogen; Y=O—, —S—; R=alkyl, hydroxyalkyl, $C_{1-4}$ aminoalkyl or $C_3$-$C_6$ polyhydroxyalkyl;
with the proviso that, when X=H, R is not methyl, and when X=H and Y=O, R is not ethyl;
process for preparing them, intermediate compounds of formula:

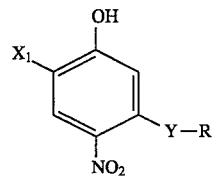

(II)

where $X_1$=halogen, Y and R have the meaning stated above;
with the proviso that, when Y=O, R is not methyl, and when R=aminoalkyl, $X_1$ can also denote hydrogen;
dyeing compositions containing one or more compounds of formula (I), and a process For dyeing human hair.

1 Claim, No Drawings

3-SUBSTITUTED PARA-AMINOPHENOLS, PROCESS FOR PREPARING THEM, THEIR USE FOR DYEING KERATINOUS FIBRES AND THE INTERMEDIATE COMPOUNDS USED IN THE PREPARATION PROCESS

This is a continuation of application Ser. No. 07/974,903, filed Nov. 12, 1992 now U.S. Pat. No. 5,364,413 which is a continuation of application Ser. No. 07/737,413, filed Jul. 29, 1991, now abandoned, which is a division of application Ser. No. 07/316,921, filed Feb. 28, 1989, now U.S. Pat. No. 5,084,067.

The invention relates to 3-substituted para-aminophenols, to a process for preparing them and to their use in dyeing compositions for dyeing keratinous fibres, and especially human hair, these dyeing compositions being used for so-called oxidation dyeing or permanent dyeing.

This dyeing process enables white hair to be dyed in a large number of hues.

The dyeing of keratinous fibres by so-called oxidation dyeing is known. This dyeing employs oxidation dye precursors, also referred to as oxidation bases, which are colourless but which, on contact with an oxidizing agent, develop a long-lasting coloration in the keratinous fibres. As oxidation dye precursors, para-phenylenediamines, ortho-phenylenediamines, para-aminophenols and ortho-aminophenols, substituted or unsubstituted, are known. These oxidation dye precursors can be mixed with one or more compounds referred to as "couplers". These couplers are generally chosen from meta-diamines, meta-aminophenols, meta-diphenols and phenols.

The subject of the invention is dyeing compositions for keratinous fibres, and especially for human hair, containing, in an aqueous vehicle, one or more oxidation dye precursors of formula (I):

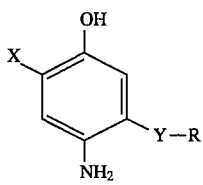

in which X denotes a hydrogen or halogen atom, Y denotes an oxygen or sulphur atom and R denotes a $C_1$–$C_4$ alkyl, $C_1$–$C_4$ hydroxyalkyl, $C_3$–$C_6$ polyhydroxyalkyl or $C_1$–$C_4$ aminoalkyl radical, with the proviso that, when X denotes a hydrogen atom and Y denotes an oxygen atom, R is not methyl; or a salt of one or more compounds of formula (I). The salts are generally hydrochlorides or sulphates.

It is preferable to use the compounds of formula (I) in which X, Y and R have the meanings stated above, with the proviso that, when X denotes a hydrogen atom and Y an oxygen atom, R does not denote an alkyl radical.

The dyeing compositions containing one or more compounds of the formula (I) enable colours which are stable to washing, to light and to adverse weather conditions to be imparted to the hair. In addition, the para-aminophenols of the formula (I) have the advantage of being very safe.

The subject of the invention is also the new compounds represented by the 3-substituted p-aminophenols of the formula (I) in which X denotes a hydrogen or halogen atom, Y denotes an oxygen or sulphur atom and R denotes a $C_1$–$C_4$ alkyl, $C_1$–$C_4$ hydroxyalkyl, $C_3$–$C_6$ polyhydroxyalkyl or $C_1$–$C_4$ aminoalkyl radical, with the proviso that.

(i) when X denotes a hydrogen atom and Y denotes an oxygen atom, R is not methyl or ethyl;

(ii) when X denotes a hydrogen atom and Y denotes a sulphur atom, R is not methyl; and their salts.

Preferred compounds are those of the formula (I) in which X, Y and R have the meanings stated above, with the proviso that, when X denotes a hydrogen atom, R is other than an alkyl radical.

The invention also relates to the process for preparing the compounds of the formula (I). These compounds are prepared in two stages from the substituted nitrophenol of the formula (III), in which X denotes hydrogen or halogen and Z denotes a halogen atom, according to the reaction scheme 1 below.

Reaction scheme 1

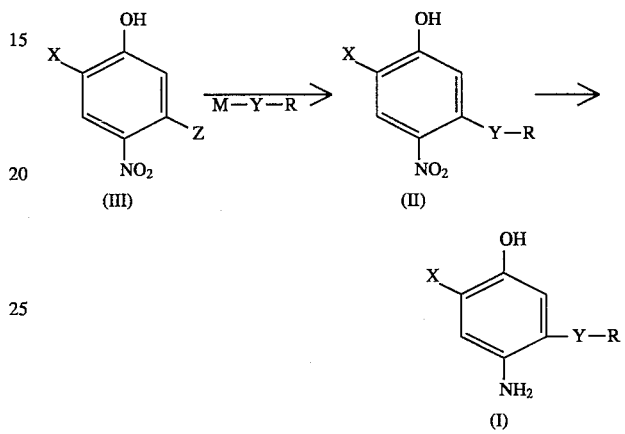

The compound (I) is obtained by reduction of the compound (II), for which compound X, Y and R have the meanings defined above. Among traditional methods of reduction, there may be mentioned reduction with sodium hydrosulphite in an alkaline medium at a temperature below 70° C., or alternatively a catalytic reduction in an aqueous-alcoholic medium under hydrogen pressure in the presence of a catalyst such as palladium on charcoal or nickel.

The compound (II) is prepared by the action of an alcoholate or thiolate of formula (IV):

M-Y-R       (IV)

in which M denotes an alkali metal or alkaline earth metal and Y and R have the meanings defined above.

The alcoholate or thiolate (IV) can be advantageously prepared in situ according to the reaction scheme 2:

Reaction scheme 2

it also being possible for the compound H-Y-R to act as a solvent.

Among solvents which can be used for preparing the compounds (II), there may be mentioned, apart from the compound H-Y-R, dioxane, N,N-dimethylformamide and N-methylpyrrolidone, used alone or mixed; in general, the reaction temperature is below 120° C.

The compound (I) in which X=H, Y=O and R=β-hydroxyethyl may also be prepared according to the reaction scheme 3, in two stages:

a) condensation of the diazonium salt of p-sulphanilic acid with 3-(β-hydroxyethoxy)phenol;

b) reduction of the azo compound obtained with sodium hydrosulphite:

Reaction scheme 3

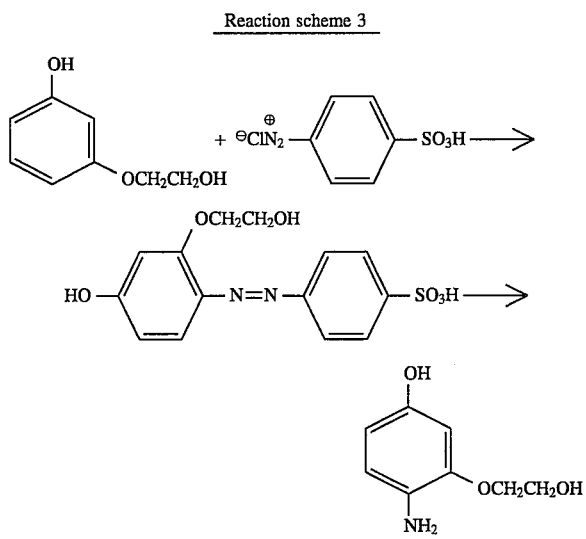

The subject of the invention is also the new para-nitrophenols of formula (II) used as intermediate compounds in the preparation of the compounds of formula (I).

In particular, the subject of the invention is substituted p-nitrophenols of the formula:

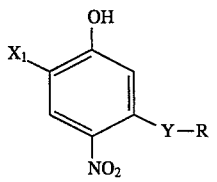
(II)

in which:

(i) Y denotes an oxygen or sulphur atom, $X_1$ denotes a hydrogen atom and R denotes a $C_{1-4}$ aminoalkyl or $C_3$–$C_6$ polyhydroxyalkyl radical, or (ii) Y denotes an oxygen atom, $X_1$ denotes a halogen atom and R denotes a $C_2$–$C_4$ alkyl radical, a $C_{1-4}$ hydroxyalkyl or $C_3$–$C_6$ polyhydroxyalkyl radical or a $C_{1-4}$ aminoalkyl radical, or (iii) Y denotes a sulphur atom, $X_1$ denotes a halogen atom and R denotes a $C_{1-4}$ alkyl, $C_{1-4}$ hydroxyalkyl, $C_3$–$C_6$ polyhydroxyalkyl or $C_{1-4}$ aminoalkyl radical;

and their salts, and especially the hydrochlorides and sulphates.

Other subjects of the invention will become apparent on reading the description, including the examples.

The invention is illustrated by the following preparation examples below.

PREPARATION EXAMPLES

EXAMPLE 1

Preparation of 4-amino-3-(β-hydroxyethoxy)phenol

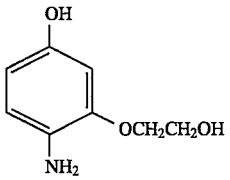

1st stage: Preparation of 3-(β-hydroxyethoxy)-4-nitrophenol

To a solution, heated on a boiling water bath, of 0.3 mole of KOH in 22.5 ml of ethylene glycol, there is added portionwise 0.1 mole (17.3 g) of 3-chloro-4-nitrophenol and then 10 ml of dioxane. Heating is maintained for 11 hours.

The phenate of the expected product is drained after the reaction medium has been cooled. It is then washed with dioxane and thereafter with ethanol, and finally dissolved in 100 ml of water. The expected product precipitates on acidification. When recrystallized from isopropanol, it melts at 167° C.

Analysis of the product obtained gives the following results:

| Analysis | Calculated for $C_8H_9NO_5$ | Found |
|---|---|---|
| % C | 48.24 | 48.19 |
| % H | 4.56 | 4.63 |
| % N | 7.03 | 6.96 |
| % O | 40.17 | 39.98 |

2nd stages: Preparation of 4-amino-3-(β-hydroxyethoxy)phenol 59 g of sodium hydrosulphite are added portionwise and with stirring to a solution consisting of 19 g of NaOH pellets and the 3-(β-hydroxyethoxy)-4-nitrophenol, prepared in the previous stage, in 160 ml of water, the temperature of the reaction medium being maintained below 70° C.

When the addition is complete, after cooling and neutralization with sulphuric acid, the expected product precipitates. It melts at 165° C. It is converted to a hydrochloride by treatment with concentrated hydrochloric acid.

The hydrochloride of the expected product is recrystallized from an aqueous-alcoholic solution of hydrochloric acid.

Analysis of the hydrochloride obtained gives the following results:

| Analysis | Calculated for $C_8H_{12}NO_3Cl$ | Found |
|---|---|---|
| % C | 46.72 | 46.57 |
| % H | 5.88 | 5.80 |
| % N | 6.81 | 6.80 |
| % O | 23.34 | 23.58 |
| % Cl | 17.24 | 17.18 |

EXAMPLE 2

Preparation of
4-amino-3-(β-hydroxyethylthio)phenol

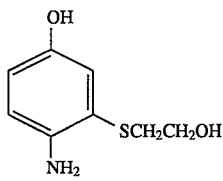

1st stage: Preparation of 3-(β-hydroxyethylthio)-4-nitrophenol 0.2 mole (34.7 g) of 3-chloro-4-nitrophenol in 20 ml of N-methylpyrrolidone is added to a solution, heated to 40° C., of 0.4 mole of KOH in 35 ml of thioethanol.

The mixture is heated for 1 hour on a boiling water bath. The reaction medium is diluted with 400 ml of ice-cold water. After neutralization with acetic acid, the expected product crystallizes.

When recrystallized from ethyl acetate, it melts at 161° C.

Analysis is of the product obtained gives the following results:

| Analysis | Calculated for $C_8H_9NO_4S$ | Found |
|---|---|---|
| % C | 44.66 | 44.60 |
| % H | 4.22 | 4.32 |
| % N | 6.51 | 6.42 |
| % O | 29.74 | 29.58 |
| % S | 14.88 | 14.77 |

2nd stage: Preparation of 4-amino-3-(β-hydroxyethylthio)phenol 118 g of sodium hydrosulphite are added portionwise and with stirring to a solution consisting of 38 g of NaOH pellets and the 3-(β-hydroxyethylthio)-4-nitrophenol, prepared in the previous stage, in 320 ml of water, the temperature being maintained below 70° C.

When the addition is complete, after cooling and neutralization with acetic acid, the expected product precipitates. It is recrystallized from ethyl acetate or acetonitrile. It melts at 85° C.

Analysis is of the product obtained gives the following results:

| Analysis | Calculated for $C_8H_{11}NO_2S$ | Found |
|---|---|---|
| % C | 51.88 | 52.01 |
| % H | 5.99 | 5.91 |
| % N | 7.56 | 7.38 |
| % O | 17.28 | 17.44 |
| % S | 17.28 | 17.26 |

EXAMPLE 3

Preparation of
4-amino-6-chloro-3-(β-hydroxyethoxy)phenol
hydrochloride

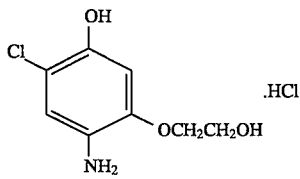

1st stage: Preparation of 6-chloro-3-(β-hydroxyethoxy)-4-nitrophenol 0.12 mole (25 g) of 3,6-dichloro-4-nitrophenol (prepared according to Fries, Annalen der Chemie 454, page 247 (1927)) 1s added to a solution, heated to 50° C., of 0.36 mole of KOH in 80 ml of ethylene glycol. The mixture is heated for 2 hours 30 minutes at 120° C.

After the mixture has cooled, the phenate of the expected product is drained and will be used directly in the next stage.

The expected product is prepared by acidifying an aqueous solution of the above phenate with acetic acid.

When recrystallized from acetonitrile, it melts at 159° C.

Analysis of the recrystallized product gives the following results:

| Analysis | Calculated for $C_8H_8NO_5Cl$ | Found |
|---|---|---|
| % C | 41.13 | 41.21 |
| % H | 3.45 | 3.49 |
| % N | 6.00 | 5.90 |
| % O | 34.24 | 33.98 |
| % Cl | 15.18 | 15.06 |

2nd stage: Preparation of 4-amino-6-chloro-3-(β-hydroxyethoxy)phenol hydrochloride 70 g of sodium hydrosulphite are added portionwise and with stirring to a solution of 32 g of 6-chloro-3-(β-hydroxyethoxy)-4-nitrophenol phenate and 75 ml of 10 N NaOH in 250 ml of water, the temperature being maintained in the region of 60°–65° C. After the mixture is cooled, the product is precipitated by neutralizing the reaction medium with acetic acid. The hydrochloride is obtained by dissolution in hydrochloric acid in the heated state and precipitation on cooling.

Analysis of the product obtained gives the following results:

| Analysis | Calculated for $C_8H_{11}NO_3Cl_2$ | Found |
|---|---|---|
| % C | 40.02 | 39.83 |
| % H | 4.62 | 4.66 |
| % N | 5.83 | 5.69 |
| % O | 19.99 | 19.71 |
| % Cl | 29.53 | 29.62 |

EXAMPLE 4

Preparation of
4-amino-6-chloro-3-(methylthio)phenol

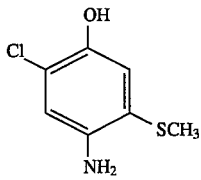

1st stage: Preparation of 6-chloro-3-methylthio-4-nitrophenol. N-methylpyrrolidone (the dye crystallizes with one mole of N-methylpyrrolidone)

0.17 mole (35.4 g) of 3,6-dichloro-4-nitrophenol is added portionwise in the course of half an hour to a suspension of 0.35 mole (25 g) of sodium thiomethylate in 50 ml of N-methylpyrrolidone, the temperature being maintained below 45° C. The mixture is heated for 30 minutes at 45° C. On dilution of the reaction medium with 400 ml of ice-cold water, followed by acidification with acetic acid, the expected product crystallizes with N-methylpyrrolidone.

When recrystallized from alcohol, it melts at 189° C.

Analysis of the product obtained gives the following results:

| Analysis | Calculated for $C_{12}H_{15}N_2O_4SCl$ | Found |
|---|---|---|
| % C | 45.21 | 45.11 |
| % H | 4.74 | 4.81 |
| % N | 8.79 | 8.97 |
| % O | 20.07 | 19.97 |
| % S | 10.06 | 9.88 |
| % Cl | 11.12 | 10.97 |

2nd stage: Preparation of 4-amino-6-chloro-3-(methylthio)phenol

The 6-chloro-3-methylthio-4-nitrophenol prepared in the preceding stage is added to a solution of 32 g of NaOH pellets in 270 ml of water, and 100 g of sodium hydrosulphite are then added rapidly without exceeding a temperature of 70° C. The mixture is stirred for a further 15 minutes after the addition is complete.

On cooling, followed by neutralization in acetic acid, the expected product is precipitated from the reaction medium.

When recrystallized from 96° strength ethanol, it melts at 188° C.

Analysis of the product obtained gives the following results:

| Analysis | Calculated for $C_7H_8NOSCl$ | Found |
|---|---|---|
| % C | 44.33 | 44.38 |
| % H | 4.25 | 4.41 |
| % N | 7.38 | 7.37 |
| % O | 8.43 | 8.68 |
| % Cl | 18.69 | 19.00 |
| % S | 16.91 | 16.78 |

EXAMPLE 5

Preparation of
4-amino-6-chloro-3-(β-aminoethylthio)phenol
dihydrochloride hydrate

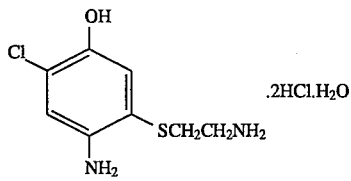

1st stage: Preparation of 3-(β-aminoethylthio)-6-chloro-4-nitrophenol hydrochloride 0.04 mole (8.3 g) of 3,6-dichloro-4-nitrophenol is added at room temperature to 0.1 mole of 2-aminoethanethiol hydrochloride and 0.14 mole of potassium carbonate in 40 ml of N-methylpyrrolidone. The above reaction medium is heated for 5 hours on a boiling water bath after 0.2 mole of KOH pellets has been added.

By adding 300 g of ice, followed by acidification to between pH 1 and 2, the unreacted starting material is precipitated. The expected product is obtained by precipitation, by adding acetic acid to the reaction medium alkalinized beforehand with 10N NaOH solution. It is recrystallized from an aqueousalcoholic mixture containing hydrochloric acid.

Analysis of the product obtained gives the following results:

| Analysis | Calculated for $C_8H_{10}N_2O_3SCl_2$ | Found |
|---|---|---|
| % C | 33.70 | 33.77 |
| % H | 3.53 | 3.63 |
| % N | 9.82 | 9.66 |
| % O | 16.83 | 16.81 |
| % S | 11.24 | 11.14 |
| % Cl | 24.87 | 24.92 |

2nd stage: Preparation of 4-amino-6-chloro-3-(β-aminoethylthio)phenol dihydrochloride hydrate 12 g of sodium hydrosulphite are added rapidly portionwise to a solution of the 3-(β-aminoethylthio)-6-chloro-4-nitrophenol hydrochloride hydrate and 4.6 g of NaOH pellets in 32 ml of water, the temperature being maintained below 70° C. After being cooled, the reaction medium is neutralized with acetic acid. By treating the gum thereby obtained with concentrated hydrochloric acid, the expected product is obtained. It is recrystallized from a mixture of hydrochloric acid and ethanol.

Analysis of the product obtained gives the following results:

| Analysis | Calculated for $C_8H_{15}Cl_3N_2O_2S$ | Found |
|---|---|---|
| % C | 31.04 | 30.99 |
| % H | 4.88 | 4.90 |
| % N | 9.04 | 8.89 |
| % O | 10.34 | 10.42 |
| % S | 10.36 | 10.25 |
| % Cl | 34.36 | 34.21 |

The dyeing compositions for keratinous fibres, and especially for human hair, according to the invention, contain at least one compound of the formula (I) in an aqueous vehicle.

The compounds of formula (I) are used in the compositions of the invention at concentrations of between 0.02 and 6%, and preferably between 0.15 and by weight relative to the total weight of the composition.

The compositions of the invention can also contain other oxidation dye precursors.

Among these oxidation dye precursors, para-phenylenediamines, para-aminophenols, ortho-phenylenediamines and ortho-aminophenols should be mentioned.

Among para-phenylenediamines, more special mention should be made of:
para-phenylenediamine,
para-tolylenediamine,
2,6-dimethyl-para-phenylenediamine,
2,6-dimethyl-3-methoxy-para-phenylenediamine,
N-(β-methoxyethyl)-para-phenylenediamine,
4-{N-[β-(β-hydroxyethoxy)ethyl]amino}aniline,
4-[N,N-bis(β-hydroxyethyl)amino]aniline,
4-[N-ethyl-N-(carbamylmethyl)amino]aniline, and also their salts.

Among para-aminophenols, more special mention should be made of:
para-aminophenol,
2-methyl-4-aminophenol,
2-chloro-4-aminophenol,
2,6-dimethyl-4-aminophenol,
2,3-dimethyl-4-aminophenol,
2,5-dimethyl-4-aminophenol,
2-hydroxymethyl-4-aminophenol,
2-(β-hydroxyethyl)-4-aminophenol, and also their salts.

Among ortho-phenylenediamines and ortho-aminophenols which may be substituted on the ring or on the amine groups, special mention should be made of 1-amino-2-hydroxybenzene, 6-methyl-1-hydroxy-2-aminobenzene and 4-methyl-1-amino-2-hydroxybenzene.

The dyeing compositions which form the subject of the present invention generally contain, in combination with the compounds (I) and optionally with para-phenylenediamines or with other para-aminophenols, couplers which give rise, by oxidative coupling with the oxidation bases, to indoanilines, indamines or indophenols having a variety of hues, which contribute to modifying and enriching with glints the basic colorations imparted to the hair by the condensation products of the oxidation bases with themselves.

Among couplers, special mention may be made of meta-diphenols, meta-aminophenols, meta-phenylenediamines, meta-acylaminophenols, meta-ureidophenols, meta-carbalkoxyaminophenols, α-naphthol and couplers possessing an active methylene group, such as β-keto compounds and pyrazolones.

Among meta-diphenols, there may be mentioned:
resorcinol,
2-methylresorcinol,
5-methylresorcinol,
2,4-dihydroxyphenoxyethanol,
resorcinol monomethyl ether,
2,4-dihydroxyanisole.

Among meta-aminophenols, there may be mentioned:
meta-aminophenol,
2-methyl-5-aminophenol,
2-methyl-5-[N-(β-hydroxyethyl)amino]phenol,
2-methyl-5-[N-(β-mesylaminoethyl)amino]phenol,
2,6-dimethyl-3-aminophenol,
6-hydroxybenzomorpholine, and their salts.

Among meta-phenylenediamines, there may be mentioned:
meta-phenylenediamine,
2,4-diaminophenoxyethanol,
2,4-dimethoxy-1,3-diaminobenzene,
1,3,5-trimethoxy-2,4-diaminobenzene,
2,4-diaminoanisole,
6-aminobenzomorpholine,
2-[N-(β-hydroxyethyl)amino]-4-aminophenoxyethanol,
4-[N-(β-hydroxyethyl)amino]-2-aminophenoxyethanol,
2-amino-4-[N-(β-hydroxyethyl)amino]anisole,
4,5-bis(β-hydroxyethoxy)-1,3-diaminobenzene,
1-(β-hydroxyethoxy)-2,4-diaminobenzene, and their salts.

Among the other couplers which are usable in the dyeing compositions of the invention, more special mention should be made of:
3,4-methylenedioxyphenol,
3,4-methylenedioxyaniline,
2-bromo-4,5-methylenedioxyphenol,
2-chloro-4,5-methylenedioxyphenol,
2-methoxy-4,5-methylenedioxyaniline.

The total weight of the oxidation dye precursors and the couplers used in the dyeing compositions according to the invention is preferably from 0.1 to 7% by weight of the total weight of the dyeing composition.

The dyeing compositions according to the invention can also contain direct dyes such as azo and anthraquinone dyes and nitro derivatives of the benzene series, which enable the hues of the colorations provided by the oxidation dye precursors and/or the couplers to be varied, or enable these colorations to be enriched with glints.

The pH of the dyeing composition is generally between 8 and 11, and preferably between 9 and 11. This pH is adjusted to the desired value using an alkalinizing agent such as ammonia solution, alkali metal carbonates or alkanolamines such as mono-, di- or triethanolamine.

The dyeing compositions according to the invention contain, in their preferred embodiment, anionic, cationic, non-ionic or amphoteric surfactants, or mixtures thereof. These surfactants are present in the compositions according to the invention in proportions of between 0.5 and 40% by weight, preferably between 2 and 30% by weight, relative to the total weight of the composition.

These compositions can also contain organic solvents, to solubilize compounds which might not be sufficiently soluble in water. Among these solvents, there may be mentioned, by way of example, $C_1$–$C_8$ alcohols such as ethanol, isopropanol, benzyl alcohol and phenylethyl alcohol; glycerol; glycols or glycol ethers such as 2-butoxyethanol, ethylene glycol, propylene glycol and diethylene glycol monoethyl ether and monomethyl ether; and also similar products and mixtures thereof. The solvents are preferably present in a proportion of between 1 and 40% by weight, and especially between 2 and 30% by weight, relative to the total weight of the composition.

The thickening agents which can be added to the compositions according to the invention are selected, in particular, from the group comprising sodium alginate, gum arabic, cellulose derivatives such as methylcellulose, hydroxyethylcellulose, hydroxypropylcellulose, hydroxymethylcellulose and carboxymethylcellulose, acrylic acid polymers and xanthan gum. It is also possible to use inorganic thickening agents such as bentonite. These thickening agents are preferably present in proportions of between 0.1 and 5% by weight, and especially between 0.5 and 3% by weight, of the total weight of the composition.

The compositions can contain antioxidants chosen, in particular, from sodium sulphite, thioglycolic acid, sodium bisulphite, ascorbic acid and hydroquinone. These antioxidants are present in the composition in proportions of between 0.05 and 1.5% by weight of the total weight of the composition.

Other adjuvants which are usable according to the invention are, for example, penetrating agents, sequestering agents, buffers and perfumes.

The dyeing compositions according to the invention maybe presented in various forms, such as in the form of liquids, creams or gels, or in any other form suitable for carrying out a dyeing of keratinous fibres, and especially human hair. They can also be packaged in aerosol cans in the presence of a propellant.

The dyeing compositions according to the invention are used in a hair dyeing process employing development with an oxidizing agent.

According to this process, the dyeing composition described above is mixed at the time of use with an oxidizing solution, in an amount sufficient for oxidizing the oxidation dye precursors, and the mixture obtained is then applied on the hair.

The oxidizing solution contains, in aqueous solution, oxidizing agents chosen from the group comprising hydrogen peroxide, urea peroxide and persalts such as ammonium persulphate. A hydrogen peroxide solution at a concentration of 6% by weight (20 volumes) is preferably used.

According to the dyeing process generally used, the mixture obtained is applied on the hair at room temperature or at a temperature not exceeding 40° C., and left in place for 10 to 40 minutes, and preferably for 15 to 30 minutes, after which the hair is rinsed, washed with shampoo, rinsed again and dried.

Another process employing the oxidation dye precursor of the formula (I) according to the invention consists in dyeing the hair in accordance with a multistage process, according to which, in a first stage, the para type oxidation dye precursor is applied by means of a composition defined above, and in a second stage, the coupler or couplers is/are applied. The oxidizing agent is present in the composition applied in the second stage, or alternatively applied on the hair itself in a third stage, the exposure, drying and washing conditions being identical to those stated for the single-stage process described above.

The invention is illustrated by the application examples below.

APPLICATION EXAMPLES

EXAMPLE A1

The following dyeing mixture is prepared:

| | |
|---|---|
| 4-Amino-3-(β-hydroxyethoxy)phenol | 0.224 g |
| p-Phenylenediamine | 0.179 g |
| Resorcinol | 0.194 g |
| m-Aminophenol | 0.356 g |
| 2-Methyl-5-[(β-hydroxyethyl)amino]phenol | 0.276 g |
| Nonylphenyl oxyethylenated with 4 moles of ethylene oxide, sold by RHONE POULENC under the name CEMULSOL NP4 | 12.00 g |
| Nonylphenyl oxyethylenated with 9 moles of ethylene oxide, sold by RHONE POULENC under the name CEMULSOL NP9 | 15.00 g |
| Oleyl alcohol polyglycerolated with 2 moles of glycerol | 1.50 g |
| Oleyl alcohol polyglycerolated with 4 moles of glycerol | 1.50 g |
| Propylene glycol | 6.00 g |
| Ethylenediaminetetraacetic acid, sold under the name TRILON B | 0.12 g |
| Ammonia solution, 22° Bé strength | 11.00 g |
| Water | qs 100.00 g |
| pH 9 | |

At the time of use, 10 g of hydrogen peroxide at a concentration of 6% by weight (20 volumes) are added. The mixture is applied for 20 minutes at 35° C. on hair which is naturally 90% white. After shampooing and rinsing, a cigar-brown coloration is Obtained.

EXAMPLE A2

The following dyeing mixture is prepared:

| | |
|---|---|
| 4-Amino-6-chloro-3-(β-hydroxyethoxy)-phenol | 0.51 g |
| 2,4-Dimethoxy-1,3-diaminobenzene dihydrochloride | 0.60 g |
| Carboxyvinyl polymer sold by the company GOODRICH CHEMICALS under the name CARBOPOL 934 | 3.00 g |
| Ethanol, 96° strength | 11.00 g |
| 2-Butoxyethanol | 5.00 g |
| Trimethylcetylammonium bromide | 2.00 g |
| Ethylenediaminetetraacetic acid, sold under the name TRILON B | 0.20 g |
| Ammonia solution, 22° Bé strength | 10.00 g |
| Sodium bisulphite 35° Bé strength | 1.00 g |
| Water | qs 100.00 g |
| pH 9 | |

At the time of use, 10 g of hydrogen peroxide at a concentration of 6% by weight are added. The mixture, applied for 20 minutes at 35° C. on bleached hair, imparts to the latter, after shampooing and rinsing, a mauve-blue coloration.

EXAMPLE A3

The following dyeing mixture is prepared:

| | |
|---|---|
| 4-Amino-3-(methylthio)phenol | 0.31 g |
| 4,5-Bis(β-hydroxyethoxy)-1,3-diamino-benzene dihydrochloride | 0.61 g |
| Nonylphenyl oxyethylenated with 4 moles of ethylene oxide, sold by RHONE POULENC under the name CEMULSOL NP4 | 12.00 g |
| Nonylphenyl oxyethylenated with 9 moles of ethylene oxide, sold by RHONE POULENC under the name CEMULSOL NP9 | 15.00 g |
| Oleyl alcohol polyglycerolated with 2 moles of glycerol | 1.50 g |
| Oleyl alcohol polyglycerolated with 4 moles of glycerol | 1.50 g |
| Propylene glycol | 6.00 g |
| Ethylenediaminetetraacetic acid, sold under the name TRILON B | 0.12 g |
| Ammonia solution, 22° Bé strength | 11.00 g |
| Water | qs 100.00 g |
| pH 9 | |

At the time of use, 9 g of hydrogen peroxide at a concentration of 6% by weight are added. The mixture, applied for 25 minutes at 35° C. on hair which is naturally 90% white, imparts to the latter, after shampooing and rinsing, a flannel-grey coloration.

EXAMPLE A4

The following dyeing mixture is prepared:

| | |
|---|---|
| 4-Amino-3-(β-hydroxyethoxy)phenol | 0.42 g |
| 1-(β-Hydroxyethoxy)-2,4-diaminobenzene dihydrochloride | 0.60 g |
| Oleyl alcohol polyglycerolated with 2 moles of glycerol | 4.50 g |
| Oleyl alcohol polyglycerolated with 4 moles of glycerol | 4.50 g |
| Oleylamine oxyethylenated with 12 moles of ethylene oxide, sold by ARMOON HESS CHEMICAL Ltd under the same ETHOMEEN 012 | 4.50 g |
| Coconut diethanolamides sold by HENKEL under the name COMPERLAN KD | 9.00 g |
| Propylene glycol | 4.00 g |

-continued

| | |
|---|---|
| 2-Butoxyethanol | 8.00 g |
| Ethanol, 96° strength | 6.00 g |
| Diethylenetriaminepentaacetic acid pentasodium salt, sold by PROTEX under the name MASQUOL DTPA | 2.00 g |
| Hydroquinone | 0.15 g |
| Sodium bisulphite solution, 35° Be strength | 1.30 g |
| Ammonia solution, 22° Bé strength | 10.00 g |
| Water | qs 100.00 g |
| pH 10 | |

At the time of use, 100 g of hydrogen peroxide at a concentration of 6% by weight are added. The mixture, applied for 20 minutes at 30° C. on bleached hair, imparts to the latter, after shampooing and rinsing, a light brown-grey coloration.

EXAMPLE A5

The following dyeing mixture is prepared:

| | |
|---|---|
| 4-Amino-3-(β-hydroxyethoxy)phenol | 0.42 g |
| 4,5-Methylenedioxy-2-methoxyaniline hydrochloride | 0.51 g |
| Oleyl alcohol polyglycerolated with 2 moles of glycerol | 4.50 g |
| Oleyl alcohol polyglycerolated with 4 moles of glycerol | 4.50 g |
| Oleylamine oxyethylenated with 12 moles of ethylene oxide, sold by ARMOON HESS CHEMICAL Ltd under the name ETHOMEEN O12 | 4.50 g |
| Coconut diethanolamides, sold by HENKEL under the name COMPERLAN KD | 9.00 g |
| Propylene glycol | 4.00 g |
| 2-Butoxyethanol | 8.00 g |
| Ethanol 96° strength | 6.00 g |
| Diethylenetriaminepentaacetic acid pentasodium salt, sold by PROTEX under the name MASQUOL DTPA | 2.00 g |
| Hydroquinone | 0.15 g |
| Sodium bisulphite solution, 35° Be strength | 1.30 g |
| Ammonia solution, 22° Bé strength | 10.00 g |
| Water | qs 100.00 g |
| pH 10 | |

At the time of use, 100 g of hydrogen peroxide at a concentration of 6% by weight are added. The mixture, applied for 20 minutes at 30° C. on hair which is naturally 90% white, imparts to the latter, after shampooing and rinsing, a light olive-brown coloration.

EXAMPLE A6

The following dyeing mixture is prepared:

| | |
|---|---|
| 4-Amino-3-(methylthio)phenol | 0.39 g |
| 2-Methyl-5-[(β-hydroxyethyl)amino]-phenol | 0.41 g |
| Oleyl alcohol polyglycerolated with 2 moles of glycerol | 4.50 g |
| Oleyl alcohol polyglycerolated with 4 moles of glycerol | 4.50 g |
| Oleylamine oxyethylenated with 12 moles of ethylene oxide, sold by ARMOON HESS CHEMICAL Ltd under the name ETHOMEEN O12 | 4.50 g |
| Coconut diethanolamides, sold by HENKEL under the name COMPERLAN KD | 9.00 g |
| Propylene glycol | 4.00 g |
| 2-Butoxyethanol | 8.00 g |
| Ethanol 96° strength | 6.00 g |
| Diethylenetraaminepentaacetic acid pentasodium salt, sold by PROTEX under the name MASQUOL DTPA | 2.00 g |
| Hydroquinone | 0.15 g |
| Sodium bisulphite solution, 35° Be strength | 1.30 g |
| Ammonia solution, 22° Bé strength | 10.00 g |
| Water | qs 100.00 g |
| pH 10 | |

At the time of use, 100 g of hydrogen peroxide at a concentration of 6% by weight are added. The mixture, applied for 20 minutes at 30° C. on bleached hair, imparts to the latter, after shampooing and rinsing, a light orange coloration.

EXAMPLE A7

The following dyeing mixture is prepared:

| | |
|---|---|
| 4-Amino-3-(β-hydroxyethylthio)phenol | 0.52 g |
| 1-(β-Hydroxyethoxy)-2,4-diaminobenzene dihydrochloride | 0.67 g |
| Cetyl/stearyl alcohol sold by CONDEA under the name ALFOL C 16/18 | 19.00 g |
| 2-Octyldodecanol sold by HENKEL under the name EUTANOL G | 4.50 g |
| Cetyl/stearyl alcohol containing 15 moles of ethylene oxide, sold by HENKEL under the name MERGITAL C.S. | 2.50 g |
| Ammonium lauryl sulphate | 10.00 g |
| Cationic polymer consisting of repeated units of formula: | 4.00 g |
| Benzyl alcohol | 2.00 g |
| Ammonia solution, 22° Bé strength | 11.00 ml |
| Ethylenediaminetetraacetic acid, sold under the name TRILON B | 1.00 g |
| Sodium bisulphite, 35° Bé strength | 1.20 g |
| Water | qs 100.00 g |
| pH 10 | |

$$\left[ \begin{array}{c} CH_3 \\ | \\ -N^{\oplus}-(CH_2)_3-N^{\oplus}-(CH_2)_6- \\ | \\ CH_3 \ Cl^{\ominus} \end{array} \begin{array}{c} CH_3 \\ | \\ \\ | \\ CH_3 \ Cl^{\ominus} \end{array} \right]$$

At the time of use, 9 g of hydrogen peroxide at a concentration of 6% by weight are added. The mixture, applied for 25 minutes at 35° C. on hair which is naturally 90% white, imparts to the latter, after shampooing and rinsing, a mink brown coloration.

We claim:

1. A dyeing composition for dyeing human hair comprising in an aqueous vehicle, one or more compounds of formula (I):

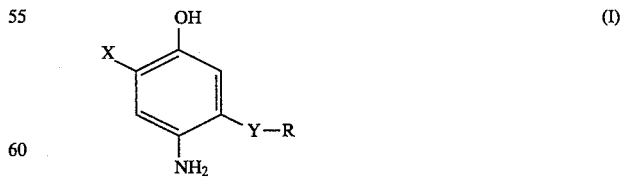

wherein

X represents hydrogen or halogen, Y represents sulfur and R represents $C_1$–$C_4$ alkyl.

* * * * *